(12) United States Patent
Frick et al.

(10) Patent No.: US 6,387,944 B1
(45) Date of Patent: May 14, 2002

(54) BENZO(B)THIEPINE-1,1-DIOXIDE DERIVATIVES, A METHOD FOR THE PRODUCTION THEREOF, MEDICAMENTS CONTAINING THESE COMPOUNDS, AND THEIR USE

(75) Inventors: Wendelin Frick, Hünstetten-Beuerbach; Alfons Enhsen, Büttelborn; Heiner Glombik, Hofheim; Hubert Heuer, Schwabenheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/719,047
(22) PCT Filed: May 28, 1999
(86) PCT No.: PCT/EP99/03701
 § 371 Date: Dec. 7, 2000
 § 102(e) Date: Dec. 7, 2000
(87) PCT Pub. No.: WO99/64410
 PCT Pub. Date: Dec. 16, 1999

(30) Foreign Application Priority Data

Jun. 10, 1998 (DE) .......................... 198 25 804

(51) Int. Cl.⁷ ...................... A61K 31/38; C07D 337/00
(52) U.S. Cl. ............................ 514/431; 549/9
(58) Field of Search .................. 549/9; 514/431

(56) References Cited

U.S. PATENT DOCUMENTS 5,994,391 A * 11/1999 Lee et al. .................. 514/431
6,096,780 A * 8/2000 Shiraishi et al. ........... 514/431
6,221,897 B1 * 4/2001 Frick et al. ................ 514/431

FOREIGN PATENT DOCUMENTS

DE       WO 97 33882       9/1997

OTHER PUBLICATIONS

Schröder, Lübke, The Peptides, Band I, New York 1965. S.XXII–XXII.
Houben–Weyl, Methoden der Organischen Chemie, Stuttgart 1974, Band XV/1 und 2.

* cited by examiner

*Primary Examiner*—Deborah C. Lambkin
(74) *Attorney, Agent, or Firm*—Finnegan, Henderson, Farabow, Garrett & Dunner, LLP

(57) ABSTRACT

The invention relates to substituted benzo(b)thiepine-1,1-dioxide derivatives and to the acid addition salts thereof. The invention relates to compounds of formula (I), wherein $R^1$, $R^2$, $R^3$, $R^4$, $R^5$ and Z have the cited descriptions, to the physiologically compatible salts, to physiologically functional derivatives, and to a method for the production thereof. The compounds are suited, for example, as hypolipidemic agents.

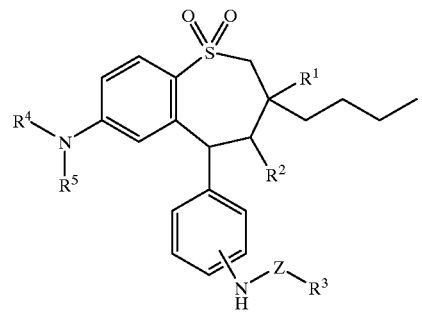

15 Claims, No Drawings

BENZO(B)THIEPINE-1,1-DIOXIDE DERIVATIVES, A METHOD FOR THE PRODUCTION THEREOF, MEDICAMENTS CONTAINING THESE COMPOUNDS, AND THEIR USE

This application is a 371 of PCT/EP99/03701 May 28, 1999

The invention relates to substituted benzo(b)thiepine 1,1-dioxide derivatives, their physiologically tolerable salts and physiologically functional derivatives.

Benzo(b)thiepine 1,1-dioxide derivatives and their use for the treatment of hyperlipidemia as well as arteriosclerosis and hypercholesterolemia have already been described [cf. PCT Application No. PCT/US97104076, publication No. WO 97/33882].

The invention was based on the object of making available further compounds which display a therapeutically utilizable hypolipidemia action. In particular, the object consisted in finding novel compounds which, compared with the compounds described in the prior art, bring about a higher fecal bile acid excretion, even at a lower dose. A dose reduction of the $ED_{200}$ value by at least the factor 5 compared with the compounds described in the prior art was particularly desirable.

The invention therefore relates to compounds of the formula I

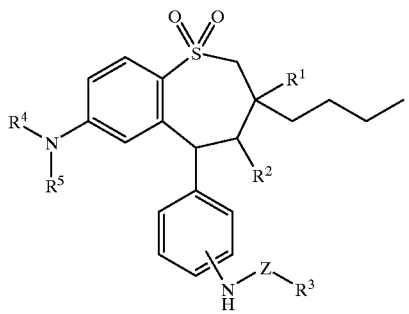

in which $R^1$ is methyl, ethyl, propyl, butyl;

$R^2$ is H, OH, $NH_2$, NH—$(C_1$–$C_6)$-alkyl;

$R^3$ is an amino acid radical, diamino acid radical, triamino acid radical, tetraamino acid radical, the amino acid radical, diamino acid radical, triamino acid radical or tetraamino acid radical optionally being mono- or polysubstituted by an amino acid protective group;

$R^4$ is methyl, ethyl, propyl, butyl;

$R^5$ is methyl, ethyl, propyl, butyl;

Z is —(C=O)$_n$—$C_0$–$C_{16}$-alkyl-, —(C=O)$_n$—$C_0$–$C_{16}$-alkyl-NH—, —(C=O)$_n$—$C_0$–$C_{16}$-alkyl-O—, —(C=O)$_n$—$C_1$–$C_{16}$-alkyl-(C=O)$_m$, a covalent bond;

n is 0 or 1;

m is 0 or 1;

and their pharmaceutically tolerable salts and physiologically functional derivatives.

Preferred compounds of the formula I are those in which one or more radical(s) has or have the following meaning:

$R^1$ is ethyl, propyl, butyl;

$R^2$ is H, OH, $NH_2$, NH—$(C_1$–$C_6)$-alkyl;

$R^3$ is an amino acid radical, diamino acid radical, the amino acid radical or diamino acid radical optionally being mono- or polysubstituted by an amino acid protective group;

$R^4$ is methyl, ethyl, propyl, butyl;

$R^5$ is methyl, ethyl, propyl, butyl;

Z is —(C=O)$_n$—$C_0$–$C_{16}$-alkyl-, —(C=O)$_n$—$C_0$–$C_{16}$-alkyl-NH—, —(C=O)$_n$—$C_0$–$C_{16}$-alkyl-O—, —(C=O)$_n$—$C_1$–$C_{16}$-alkyl-(C=O)$_m$, a covalent bond;

n is 0 or 1;

m is 0 or 1;

and their pharmaceutically tolerable salts.

Particularly preferred compounds of the formula I are those in which one or more radical(s) has or have the following meaning:

$R^1$ is ethyl, butyl;

$R^2$ is OH;

$R^3$ is a diamino acid radical, the diamino acid radical optionally being mono- or polysubstituted by an amino protective group;

$R^4$ is methyl;

$R^5$ is methyl;

Z is —(C=O)—$C_0$–$C_4$-alkyl, a covalent bond;

and their pharmaceutically tolerable salts.

On account of their higher water solubility compared with the starting or base compounds, pharmaceutically tolerable salts are particularly suitable for medicinal applications. These salts must have a pharmaceutically tolerable anion or cation. Suitable pharmaceutically tolerable acid addition salts of the compounds according to the invention are salts of inorganic acids, such as hydrochloric acid, hydrobromic, phosphoric, metaphosphoric, nitric, sulfonic and sulfuric acid, and of organic acids, such as, for example, acetic acid, benzenesulfonic, benzoic, citric, ethanesulfonic, fumaric, gluconic, glycolic, isothionic, lactic, lactobionic, maleic, malic, methanesulfonic, succinic, p-toluenesulfonic, tartaric and trifluoroacetic acid. For medicinal purposes, the chlorine salt is particularly preferably used. Suitable pharmaceutically tolerable basic salts are ammonium salts, alkali metal salts (such as sodium and potassium salts) and alkaline earth metal salts (such as magnesium and calcium salts).

Salts with an anion which is not pharmaceutically tolerable are likewise included in the scope of the invention as useful intermediates for the preparation or purification of pharmaceutically tolerable salts and/or for use in nontherapeutic, for example in-vitro, applications.

The term "physiologically functional derivative" used here indicates any physiologically tolerable derivative of a compound according to the invention, e.g. an ester which, on administration to a mammal, such as, for example, man, is able (directly or indirectly) to form such a compound or an active metabolite thereof.

A further aspect of this invention are prodrugs of the compounds according to the invention. Such prodrugs can be metabolized in vivo to give a compound according to the invention. These prodrugs can themselves be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) according to formula (I)" refer to compound(s) of the formula (I) as described above, and also their salts, solvates and physiologically functional derivatives as described herein.

The amount of a compound according to formula (I) which is necessary in order to achieve the desired biological effect is dependent on a number of factors, e.g. the specific compound selected, the intended use, the manner of administration and the clinical condition of the patient. In general, the daily dose is in the range from 0.1 mg to 100 mg (typically from 0.1 mg and 50 mg) per day per kilogram of body weight, e.g. 0.1–10 mg/kg/day. Tablets or capsules can contain, for example, from 0.01 to 100 mg, typically from 0.02 to 50 mg. In the case of pharmaceutically tolerable salts, the abovementioned weight data relate to the weight of the benzo(b)thiepine ion derived from the salt. For the prophylaxis or therapy of the abovementioned conditions, the compounds according to formula (I) can be used themselves as the compound, but preferably they are present in the form of a pharmaceutical composition with a tolerable excipient. The excipient must of course be tolerable in the sense that it is compatible with the other constituents of the composition and is not harmful to the health of the patient. The excipient can be a solid or a liquid or both and is preferably formulated with the compound as an individual dose, for example as a tablet, which can contain from 0.05% to 95% by weight of the active compound. Further pharmaceutically active substances can also be present, including further compounds according to formula (I). The pharmaceutical compositions according to the invention can be prepared by one of the known pharmaceutical methods, which essentially consists in mixing the constituents with pharmacologically tolerable excipients and/or auxiliaries.

Pharmaceutical compositions according to the invention are those which are suitable for oral and peroral (e.g. sublingual) administration, although the most suitable manner of administration is dependent-in each individual case on the nature and severity of the condition to be treated and on the type of the compound according to formula (I) used in each case. Coated formulations and coated delayed-release formulations are also included in the scope of the invention. Acid-resistant and enteric formulations are preferred. Suitable enteric coatings include cellulose acetate phthalate, polyvinal acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets, which in each case contain a specific amount of the compound according to formula (I); as a powder or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the excipient (which can consist of one or more additional constituents) are brought into contact. In general, the compositions are prepared by uniform and homogeneous mixing of the active compound with a liquid and/or finely divided solid excipient, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (number of) surface-active/dispersing agent(s) in a suitable machine. Shaped tablets can be produced by shaping the pulverulent compound moistened with an inert liquid diluent in a suitable machine.

Pharmaceutical compositions which are suitable for per-oral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

The invention furthermore relates both to isomer mixtures of the formula I, and the pure stereoisomers of the formula I, as well as diastereomer mixtures of the formula I and the pure diastereomers. The separation of the mixtures is carried out chromatographically.

Preferred racemic and enantiomerically pure compounds of the formula I are those having the following structure:

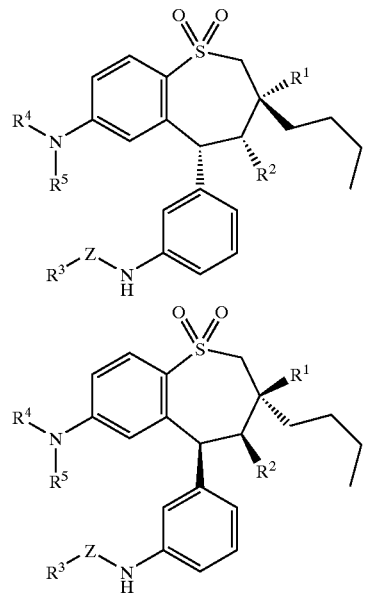

The term amino acids or amino acid residues means, for example, the stereoisomeric forms, i.e. D or L forms, of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophane | methionine | valine |
| tyrosine | asparagine | |
| 2-aminoadipic acid | 2-aminoisobutyric acid | |
| 3-aminoadipic acid | 3-aminoisobutyric acid | |
| beta-alanine | 2-aminopimelic acid | |
| 2-aminobutyric acid | 2,4-diaminobutyric acid | |
| 4-aminobutyric acid | desmosine | |
| piperidinic acid | 2,2-diaminopimelic acid | |
| 6-aminocaproic acid | 2,3-diaminopropionic acid | |
| 2-aminoheptanoic acid | N-ethylglycine | |
| 2-(2-thienyl)glucine | 3-(2-thienyl)alanine | |
| penicillamine | sarcosine | |
| N-ethylasparagine | N-methylisoleucine | |
| hydroxylysine | 6-N-methyllysine | |
| allo-hydroxylysine | N-methylvaline | |
| 3-hydroxyproline | norvaline | |
| 4-hydroxyproline | norleucine | |
| isodesmosine | ornithine | |
| allo-isoleucine | | |
| N-methylglycine | | |

The brief notation for the amino acids follow the generally customary notation (cf. Schröder, Lübke, The Peptides, Band I, New York 1965, pages XXII–XXIII; Houben-Weyl, Methoden der Organischen Chemie [Methods of Organic Chemistry], Volume XV/1 and 2, Stuttgart 1974). The amino acid pGlu is pyroglytamyl, Nal is 3-(2-naphthyl)alanine, azagly-$NH_2$ is a compound of the formula $NH_2$–HN—$CONH_2$ and D-Asp is the D form of aspartic acid. According to their chemical nature, peptides are acid amides and decompose into amino acids on hydrolysis.

Diamino acid residue, triamino acid residue, tetraamino acid residue are understood as meaning peptides which are synthesized from 2 to 4 of the abovementioned amino acids.

Suitable protective groups (see, for example, T. W. Greene, "Protective Groups in Organic Synthesis") employed for amino acids are primarily:
Arg(Tos), Arg(Mts), Arg(Mtr), Arg(PMV), Asp(OBzl), Asp (OBut), Cys(4-MeBzl), Cys(Acm), Cys(SBut), Glu (OBzl), Glu(OBut), His(Tos), His(Fmoc), His(Dnp), His (Trt), Lys(Cl-2), Lys(Boc), Met(O), Ser(Bzl), Ser(But), Thr(Bzl), Thr(But), Trp(Mts), Trp(CHO), Tyr(Br-Z), Tyr (Bzl) or Tyr(but).

Amino protective groups used are preferably the benzyloxycarbonyl(Z) radical which is removable by catalytic hydrogenation, the 2-(3,5-dimethyloxy-phenyl)prop-2-yloxycarbonyl (Ddz) or trityl (Trt) radical which can be cleaved by weak acids and the 9-fluorenylmethyloxycarbonyl (Fmoc) radical which can be removed by secondary amines.

The invention furthermore relates to a process for the preparation of benzo(b)thiepine 1,1-dioxide derivatives of the formula I:

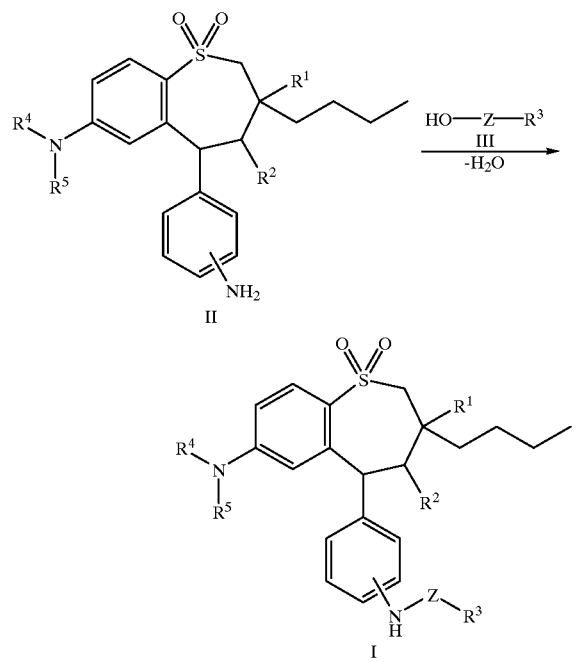

A process for the preparation of compounds of the formula I, which comprises reacting an amine of the formula II, in which $R^1$, $R^2$, $R^4$ and $R^5$ have the meanings indicated for formula I, with a compound of the formula III, in which $R^3$ and Z have the meanings indicated for formula I, with elimination of water to give a compound of the formula I and optionally converting the compound of the formula I obtained into a physiologically tolerable salt or a physiologically functional derivative. If the radical $R^3$ is a monoamino acid, this radical can optionally also still be lengthened stepwise so as to give the diamino acid radical, triamino acid radical or tetraamino acid radical after bonding to the amine of the formula II.

The compounds of the formula I and their pharmaceutically tolerable salts and physiologically functional derivatives are ideal pharmaceuticals for the treatment of lipid metabolism disorders, in particular of hyperlipidemia. The compounds of the formula I are likewise suitable for influencing the serum cholesterol level and for the prevention and treatment of arteriosclerotic symptoms. The compounds can optionally also be administered in combination with statins, such as, for example, simvastatatin, fluvastatin, pravastatin, cerivastatin, lovastatin or atorvastin. The following findings confirm the pharmacological efficacy of the compounds according to the invention.

The biological testing of the compounds according to the invention was carried out by determination of the $ED_{200}$ excretion. This testing investigates the action of the compounds according to the invention on the bile acid transport in the ileum and the fecal excretion of bile acids in the rat after oral administration twice daily. The diastereomer mixtures of the compounds were tested.

The test was carried out as follows:

1) Preparation of the Test and Reference Substances

The following recipe was used for the formulation of an aqueous solution: the substances were dissolved in adequate volumes of an aqueous solution comprising Solutol (=polyethylene glycol 600 hydroxystearate; BASF, Ludwigshafen, Germany; Batch No. 1763), so that a final concentration of 5% of Solutol is present in the aqueous solution. The solutions/suspensions were administered orally in a dose of 5 ml/kg.

2) Experimental Conditions

Male Wistar rats (Kastengrund, Hoechst AG, weight range 250–350 g) were kept in groups of 6 animals each and received a standard feed mixture (Altromin, Lage, Germany) from 10 days before the start of treatment (day 1) with a reversed day/night rhythm (4.00–16.00 dark, 16.00–4.00 light). Three days before the start of the experiment (day 0), the animals were divided into groups of 4 animals each.

Division of the animals into treatment groups:

| Number of the group | Animal No./ Analysis No. | Test substance[1] | Dose (mg/kg/d) |
|---|---|---|---|
| 1 | 1–4 | negative control | Vehicle |
| 2 | 5–8 | Test substance Dose 1 | 2 × 0.008 |
| 3 | 9–12 | Test substance Dose 2 | 2 × 0.02 |
| 4 | 13–16 | Test substance Dose 3 | 2 × 0.1 |
| 5 | 17–20 | Test substance Dose 4 | 2 × 0.5 |

[1]dissolved/suspended in 5% Solutol HS 15/0.4% starch mucilage

3) Experimental Course

After intravenous or subcutaneous administration of 5 µCi of $^{14}$C-taurocholate per rat (day 0), the vehicles or test substances were given at 7.00–8.00 and at 15.00–16.00 on the following day (day 1) (treatment for one day).

Stool samples for the analysis of $^{14}$C-taurocholate were taken every 24 hours directly after the administration of the morning dose. The feces were weighed, stored at –18° C. and later suspended in 100 ml of demineralized water and homogenized (Ultra Turrax, Janke & Kunkel, IKA-Werk). Aliquot parts (0.5 g) were weighed and combusted on combustion lids (Combusto Cones, Canberra Packard) in a combustion apparatus (Tri Carb® 307 combuster Canberra Packard GmbH, Frankfurt am Main, Germany). The resulting [14]$CO_2$ was absorbed with Carbo-Sorb® (Canberra Packard). The following $^{14}$C radioactivity measurements were determined after addition of the scintillator (Perma-Fluor complete scintillation cocktail No. 6013187, Packard) to the samples with the aid of liquid scintillation counting (LSC). The fecal excretion of $^{14}$C-taurocholic acid was calculated as a cumulative and/or percentage residual radioactivity (see below).

4) Observations and Measurements

The fecal excretion of $^{14}$C-TCA was determined in combusted aliquot parts of the stool samples taken at 24-hour intervals, calculated as the "cumulative percentage" of the administered activity and expressed as a % of the residual activity (=remaining activity, i.e. administered activity minus the already excreted activity). For the calculation of the dose-response curves, the excretion of $^{14}$C taurocholic acid was expressed as a percentage proportion of the corresponding values of the control group (treated with vehicle). The ED$_{200}$, i.e. the dose which increases the fecal excretion of $^{14}$C taurocholic acid to 200% of the control group, is calculated from a sigmoid or linear dose-response curve by interpolation. The calculated ED$_{200}$ corresponds to a dose which doubles the fecal excretion of bile acids.

5) Results

Table 1 shows measurements of the ED$_{200}$ excretion.

TABLE 1

| Compounds from Example | ED$_{200}$ excretion (mg/kg/d) p.o. |
|---|---|
| 4 | 0.04 |
| Comparison Examples | |
| 1 | 0.8 |
| 2 | 1.0 |
| 3 | 0.9 |

6) Discussion

It can be inferred from the measured data that the compounds of the formula I according to the invention have an action which is better by the factor 20 compared with the compounds described in the prior art.

The following Examples serve to illustrate the invention in greater detail without restricting same to products and embodiments described in the Examples.

Example 4

8a

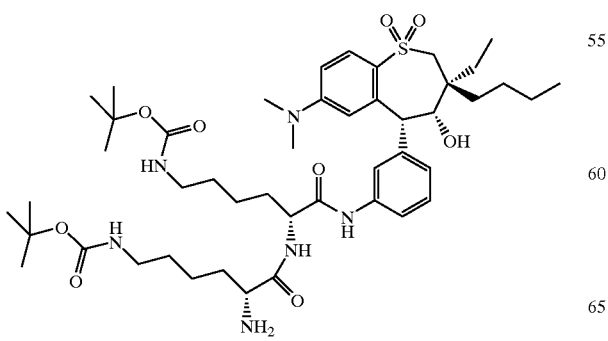

-continued

8b

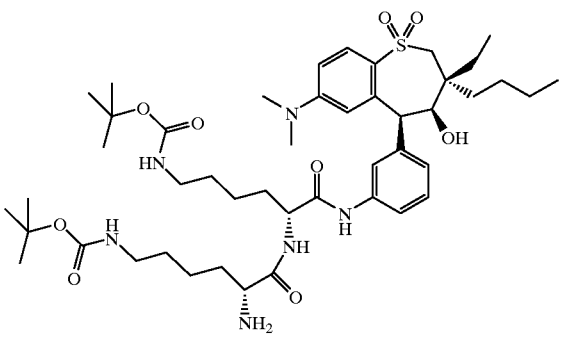

C$_{46}$H$_{74}$N$_6$O$_9$S (887.20). MS (M+H)$^+$=887.5

Comparison Example from PCT/US97/04076

Comparison Example 1

1a

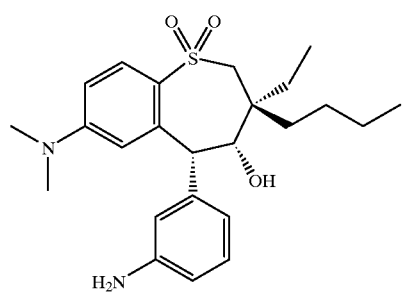

1b

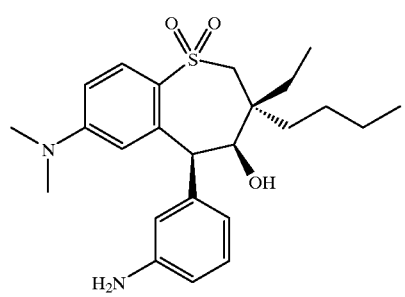

Comparison Example 2

9a

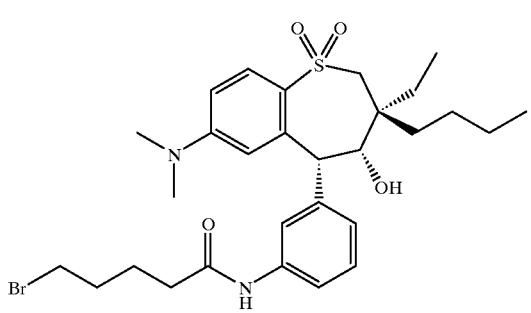

Reaction Scheme 1
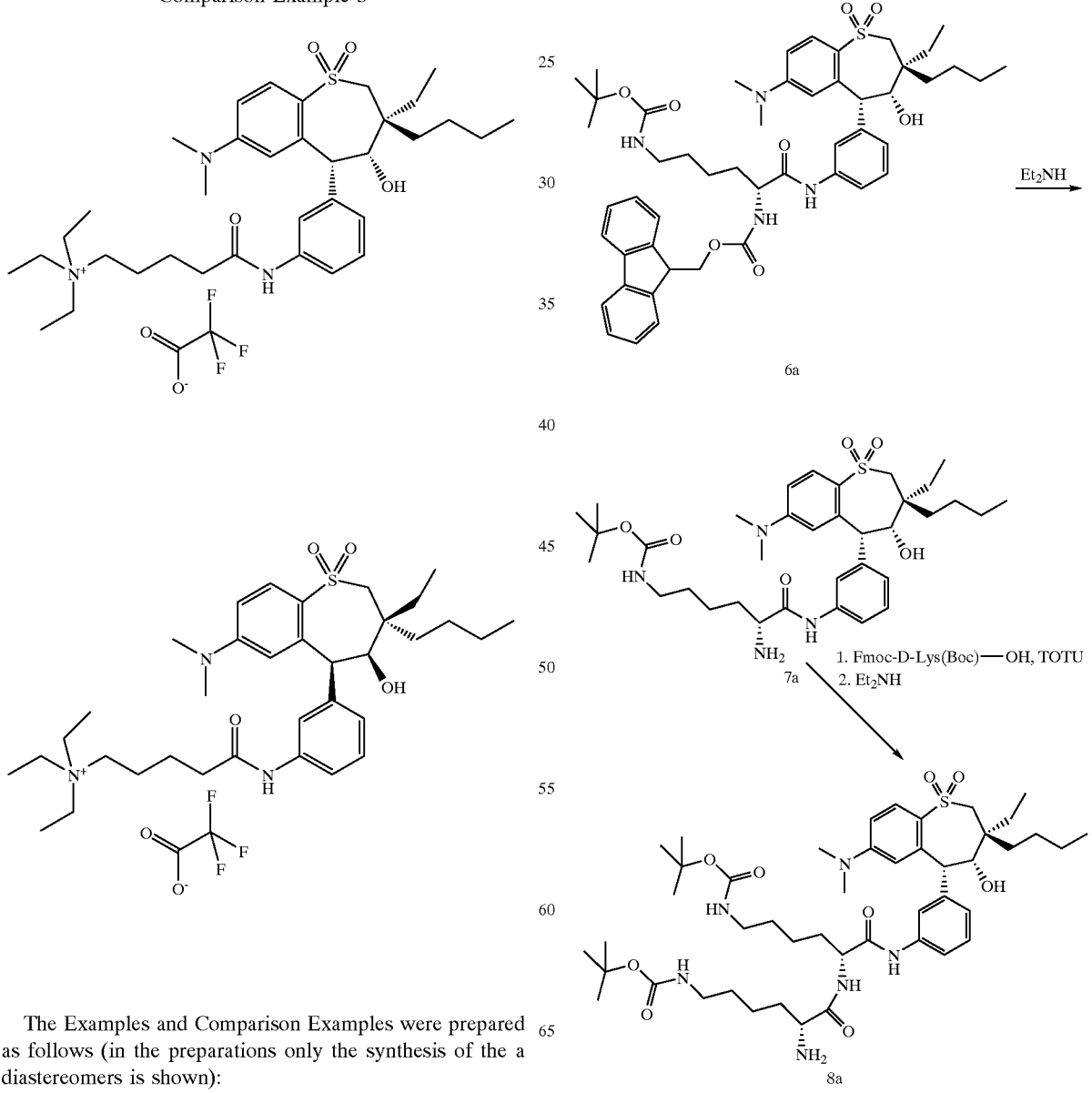
Comparison Example 3
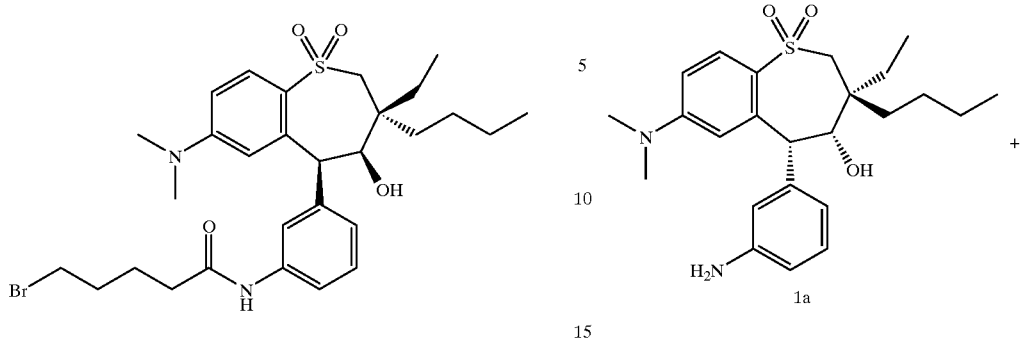
The Examples and Comparison Examples were prepared as follows (in the preparations only the synthesis of the a diastereomers is shown):

Synthesis of Compound 6 as a Diastereomer Mixture 150 mg (0.35 mmol) of 1a/b and 245 mg (0.52 mmol) of Fmoc-D-Lys(Boc)-OH 5 (Fluka) in 6 ml of DMF are reacted with 169 mg of TOTU, 74 mg of oxime and 0.5 ml of NEM anagously to the synthesis of compound 3. Yield 290 mg (94%) of 6a/b as an amorphous solid. TLC (ethylene acetate/n-heptane 2:1). $R_f$=0.6. $C_{50}H_{64}N_4O_8S$ (881.15). MS $(M+H)^+$=881.5.

Synthesis of Compound 7 as a Diastereomer Mixture 285 mg (0.32 mmol) of 6a/b are dissolved in 5 ml of DMF. After an addition of 0.6 ml of diethylamine, the mixture is allowed to stand for 30 minutes. Working-up is carried out analogously to the synthesis of compound 3. Yield 173 mg (81%) of 7a/b as an amorphous solid. TLC (methylene chloride/methanol 15:1). $R_f$=0.2, starting material 6a/b $R_f$=0.4. $C_{35}H_{54}N_4O_6S$ (658.91). MS $(M+H)^+$=659.4.

Synthesis of Compound 8 as a Diastereomer Mixture 168 mg (0.25 mmol) of 7a/b are reacted analogously to the synthesis of compound 6 and 7 and 169 mg (75% over two stages) of 8a/b is obtained as an amorphous solid. TLC (methylene chloride/methanol 9:1). $R_f$=0.3. $C_{46}H_{74}N_6O_9S$ (887.20). MS $(M+H)^+$=887.5.

What is claimed is:

1. A compound of the formula I

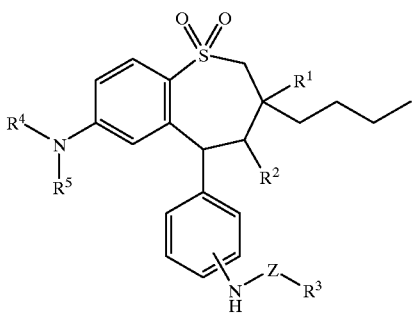

in which $R^1$ is methyl, ethyl, propyl, butyl;

$R^2$ is H, OH, $NH_2$, NH—$(C_1-C_6)$-alkyl;

$R^3$ is an amino acid radical, diamino acid radical, triamino acid radical, tetraamino acid radical, the amino acid radical, diamino acid radical, triamino acid radical or tetraamino acid radical optionally being mono- or polysubstituted by an amino acid protective group;

$R^4$ is methyl, ethyl, propyl, butyl;

$R^5$ is methyl, ethyl, propyl, butyl;

Z is —$(C=O)_n$—$C_0$-$C_{16}$-alkyl, —$(C=O)_n$—$C_0$-$C_{16}$-alkyl-NH—, —$(C=O)_n$—$C_0$-$C_{16}$-alkyl-O—, —$(C=O)_n$—$C_1$-$C_{16}$-alkyl-$(C=O)_m$, a covalent bond;

n is 0 or 1;

m is 0 or 1;

or its pharmaceutically tolerable salts and physiologically functional derivatives.

2. A compound of the formula I as claimed in claim 1, wherein one or more of the radicals has or have the following meaning:

$R^1$ is ethyl, propyl, butyl;

$R^2$ is H, OH, $NH_2$, NH—$(C_1-C_6)$-alkyl;

$R^3$ is an amino acid radical, diamino acid radical, the amino acid radical or diamino acid radical optionally being mono- or polysubstituted by an amino acid protective group;

$R^4$ is methyl, ethyl, propyl, butyl;

$R^5$ is methyl, ethyl, propyl, butyl;

Z is —$(C=O)_n$—$C_0$-$C_{16}$-alkyl-, —$(C=O)_n$—$C_0$-$C_{16}$-alkyl-NH—, —$(C=O)_n$—$C_0$-$C_{16}$-alkyl-O—, —$(C=O)_n$—$C_1$-$C_{16}$-alkyl-$(C=O)_m$, a covalent bond;

n is 0 or 1;

m is 0 or 1;

or its pharmaceutically tolerable salts.

3. A compound of the formula I as claimed in claim 1 or 2, wherein one or more of the radicals has or have the following meaning:

$R^1$ is ethyl, butyl;

$R^2$ is OH;

$R^3$ is a diamino acid radical, the diamino acid radical optionally being mono- or polysubstituted by an amino protective group;

$R^4$ is methyl;

$R^5$ is methyl;

Z is —$(C=O)$—$C_0$-$C_4$-alkyl, a covalent bond;

its pharmaceutically tolerable salts.

4. A process for the preparation of compounds of the formula I as claimed in claim 1, which comprises reacting, according to the following equation,

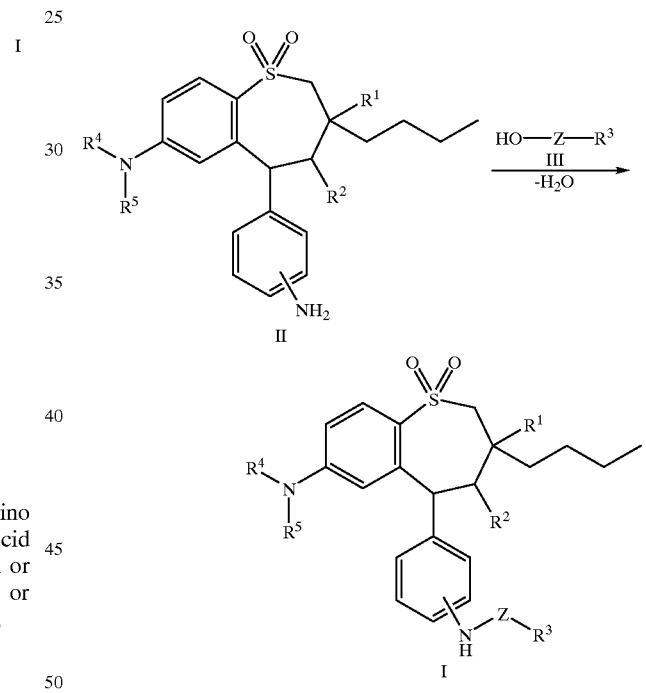

an amine of the formula II, in which $R^1$, $R^2$, $R^4$ and $R^5$ have the meanings indicated for formula I, with a compound of the formula III, in which $R^3$ and Z have the meanings indicated for formula I, with elimination of water to give a compound of the formula I and optionally converting the compound of the formula I obtained into a physiologically tolerable salt or a physiologically functional derivative.

5. A pharmaceutical, comprising one or more of the compounds as claimed in claim 1.

6. A pharmaceutical comprising one or more of the compounds as claimed in claim 1 and one or more statins.

7. A compound as claimed in one or more of claims 1 or 2 for use as a medicament for the treatment of lipid metabolism disorders.

8. A process for the production of a pharmaceutical comprising one or more of the compounds as claimed in claim 1 which comprises mixing the active compound with a pharmaceutically suitable excipient and bringing this mixture into a form suitable for administration.

9. A compound as claimed in claim 3 for use as a medicament for the treatment of lipid metabolism disorders.

10. A medicament for the treatment of hyperlipidemia comprising one or more compounds as claimed in claims 1 or 2.

11. A medicament for influencing serum cholesterol level comprising one or more compounds as claimed in claims 1 or 2.

12. A medicament for the prevention of arteriosclerotic symptoms comprising one or more compounds as claimed in claims 1 or 2.

13. A medicament for the treatment of hyperlipidemia comprising one or more compounds as claimed in claim 3.

14. A medicament for influencing serum cholesterol level comprising one or more compounds as claimed in claim 3.

15. A medicament for the prevention of arteriosclerotic symptoms comprising one or more compounds as claimed in claim 3.

* * * * *

UNITED STATES PATENT AND TRADEMARK OFFICE
CERTIFICATE OF CORRECTION

PATENT NO. : 6,387,944 B1
DATED : May 14, 2002
INVENTOR(S) : Wendelin Frick et al.

It is certified that error appears in the above-identified patent and that said Letters Patent is hereby corrected as shown below:

Column 12,
Line 59, "pharmaceutical," should read -- pharmaceutical --.
Line 63, "in one or more of" should read -- in --.

Column 13,
Line 1, "claim 1" should read -- claim 1, --.

Signed and Sealed this

Twenty-second Day of October, 2002

*Attest:*

*Attesting Officer*

JAMES E. ROGAN
*Director of the United States Patent and Trademark Office*